US012446932B2

(12) United States Patent
Alsup

(10) Patent No.: US 12,446,932 B2
(45) **Date of Patent: *Oct. 21, 2025**

(54) CERVICAL PLATE AND SCREW LOCKING MECHANISM

(71) Applicant: Vy Spine LLC, Bountiful, UT (US)

(72) Inventor: Jeremy S. Alsup, Bountiful, UT (US)

(73) Assignee: Vy Spine LLC, Bountiful, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/508,020

(22) Filed: Nov. 13, 2023

(65) Prior Publication Data

US 2024/0081882 A1 Mar. 14, 2024

Related U.S. Application Data

(63) Continuation of application No. 16/530,238, filed on Aug. 2, 2019, now Pat. No. 11,813,004.

(60) Provisional application No. 62/714,509, filed on Aug. 3, 2018.

(51) Int. Cl.
*A61B 17/80* (2006.01)

(52) U.S. Cl.
CPC ................................ *A61B 17/8042* (2013.01)

(58) Field of Classification Search
CPC .................................................. A61B 17/8042
See application file for complete search history.

(56) References Cited

U.S. PATENT DOCUMENTS

2021/0145487 A1* 5/2021 Swanhn ............ A61B 17/7059

* cited by examiner

*Primary Examiner* — Suba Ganesan
(74) *Attorney, Agent, or Firm* — Fox Rothschild LLP

(57) ABSTRACT

The present invention generally relates to medical hardware for use in spinal stabilization, spinal fusion, spinal alignment and similar spinal surgical procedures. Specifically, the invention relates to a cervical plate with an integrated screw lock mechanism.

20 Claims, 7 Drawing Sheets

CERVICAL PLATE AND SCREW LOCKING MECHANISM

CROSS-REFERENCE TO RELATED APPLICATIONS

The present application is a continuation of U.S. application Ser. No. 16/530,238, entitled "Cervical Plate and Screw Locking Mechanism", filed on Aug. 2, 2019, which claims the benefit of U.S. Provisional App. No. 62/714,509 entitled "Cervical Plate and Screw Locking Mechanism" filed on Aug. 3, 2018, the entire disclosure of each of which is hereby incorporated by reference herein.

FIELD OF THE INVENTION

The present invention generally relates to medical hardware for use in spinal stabilization, spinal fusion, spinal alignment and similar spinal surgical procedures. Specifically, the invention relates to a cervical plate with an integrated screw lock mechanism.

BACKGROUND

Many medical devices have been developed for use in spinal fixation. Generally, cervical plates are used to facilitate the decompression, immobilization and stabilization of vertebrae in patients by implanting several bone screws through a cervical plate and into the desired vertebrae. A variety of cervical plates have been developed, having their advantages and disadvantages. An inherent disadvantage posed by traditional cervical plate devices, and the placement procedures for such devices, is the possible dislodgement, untightening, or general loosening of the bone screws used during such procedures. Furthermore, current cervical plates require additional tools and time to secure the locking mechanism to the bone screw and leave the locking mechanism exposed, which can cause irritation or injury to surrounding tissue.

Therefore, there is a need in the art for a cervical plate having a screw lock to secure the bone screws to avoid their loosening or dislodgement and enable a surgeon or operating physician to more easily perform cervical plate implantation procedures. These and other features and advantages of the present invention will be explained and will become obvious to one skilled in the art through the summary of the invention that follows.

SUMMARY OF THE INVENTION

The present invention is a medical device and a method of manufacture and use thereof. In some embodiments, the medical device primarily includes a cervical plate having a screw locking mechanism.

According to an embodiment of the present invention, a cervical plate assembly comprises a plate body having an anterior surface and a posterior surface opposite the anterior surface, the plate body further comprising: at least a pair of bone screw holes extending through the plate body from the anterior surface through the posterior surface, each of the bone screw holes having a substantially circular side wall, with a screw lock receiving channel extending between and connecting a first screw hole and a second screw hole, and a screw lock body located in the screw lock receiving channel having a first screw locking edge connected by at least one compliant linking member to a second screw locking edge, wherein the first screw locking edge partially extends into a first bone screw hole and the second screw locking edge partially extends into a second screw hole, and wherein each screw locking edge engages with a bone screw and secures the bone screw to the plate body.

According to an embodiment of the present invention, a cervical plate assembly comprises a plate body having an anterior surface and a posterior surface opposite the anterior surface, the plate body further comprising: at least a pair of bone screw holes extending through the plate body from the anterior surface through the posterior surface, each of the bone screw holes having a substantially circular side wall, with a screw lock receiving channel extending between and connecting a first screw hole and a second screw hole, and a screw lock body located in the screw lock receiving channel having a first screw locking edge connected to a second screw locking edge by a compliant linking member comprised of two serpentine elements, wherein the first screw locking edge partially extends into a first bone screw hole and the second screw locking edge partially extends into a second screw hole, and wherein each screw locking edge engages with a bone screw and secures the bone screw to the plate body.

According to an embodiment of the present invention, a screw lock assembly comprises a screw lock body having a first screw locking edge connected to a second screw locking edge by a compliant linking member comprised of two serpentine elements, wherein each screw locking edge includes a plate stop tab, wherein the first screw locking edge partially extends into a first bone screw hole and the second screw locking edge partially extends into a second screw hole, and wherein each screw locking edge engages with a bone screw and secures the bone screw to a cervical plate body.

BRIEF DESCRIPTION OF THE DRAWINGS

Accompanying this written specification is a collection of drawings of exemplary embodiments of the present invention. One of ordinary skill in the art would appreciate that these are merely exemplary embodiments, and additional and alternative embodiments may exist and still be within the spirit of the invention as described herein.

DETAILED SPECIFICATION

Figure 1:
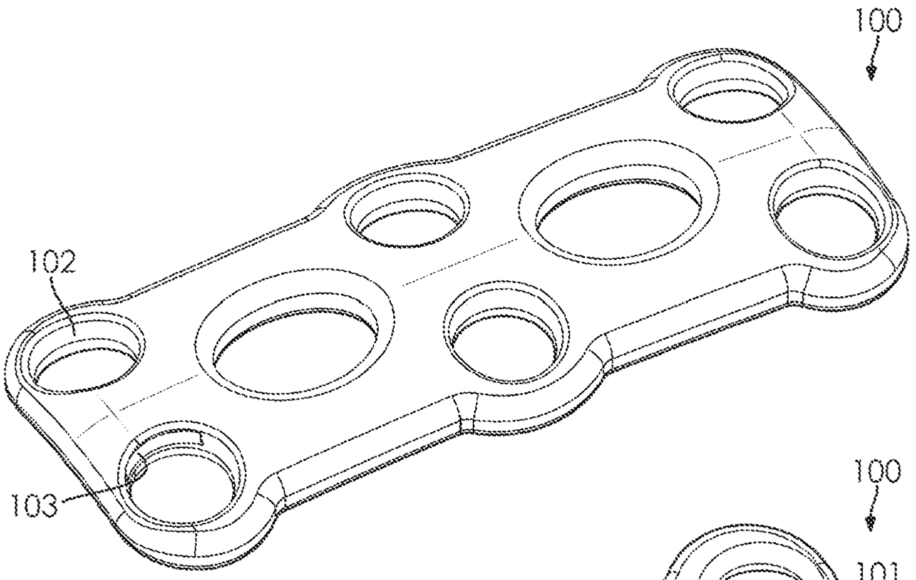
FIG. 1 is a top perspective view of a cervical plate with a screw lock, in accordance with an embodiment of the present invention.
Figure 2:
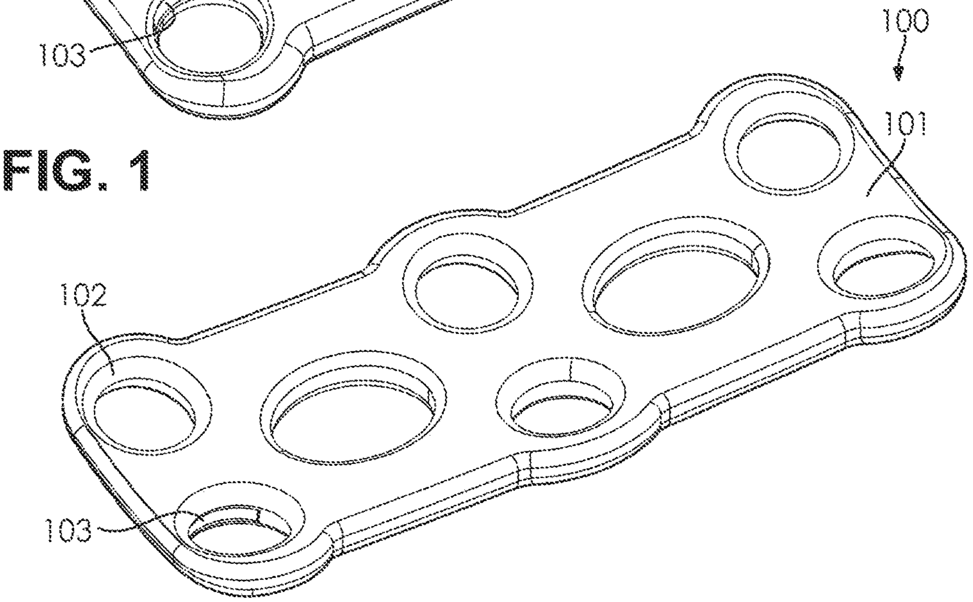
FIG. 2 is a bottom perspective view of a cervical plate with a screw lock, in accordance with an embodiment of the present invention.
Figure 3:
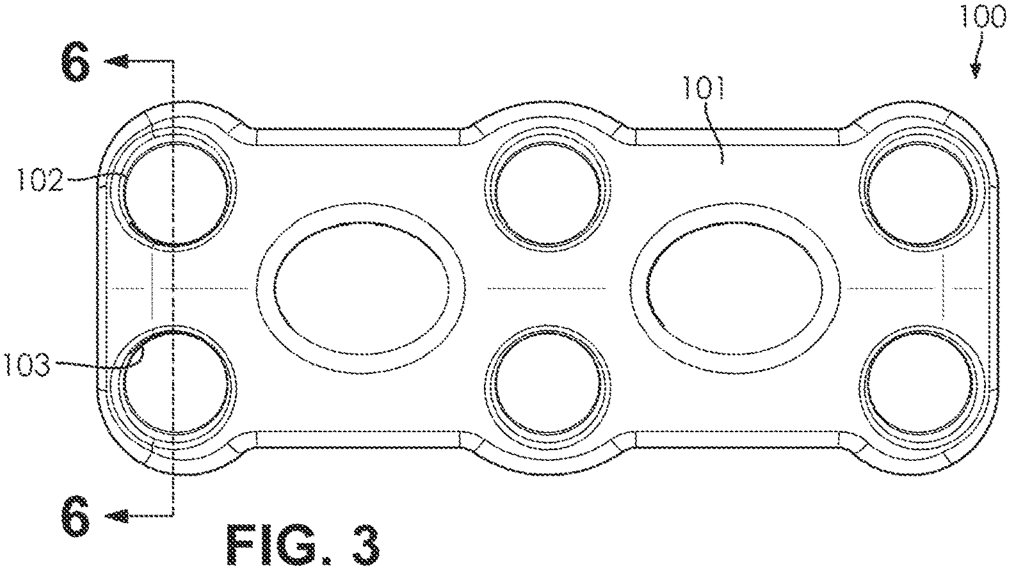
FIG. 3 is a top view of a cervical plate with a screw lock, in accordance with an embodiment of the present invention.
Figure 4:
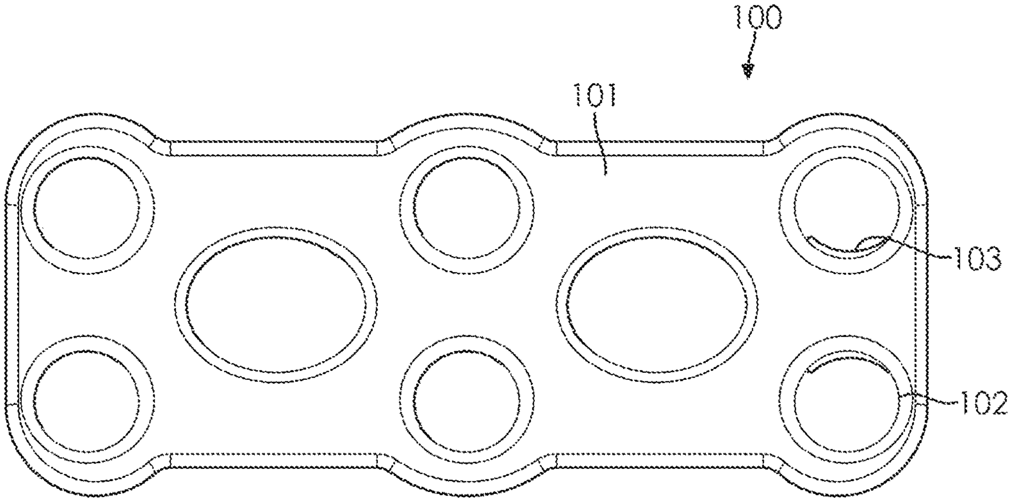
FIG. 4 is a bottom view of a cervical plate with a screw lock, in accordance with an embodiment of the present invention.

The present invention generally relates to medical hardware for use in spinal stabilization, spinal fusion, spinal alignment and similar spinal surgical procedures. Specifically, the invention relates to a cervical plate with an integrated screw lock mechanism.

According to an embodiment of the present invention, the spinal fusion surgical hardware described herein comprises a cervical plate and one or more screw locks which collectively serve as a locking cover plate for bone screws. In a preferred embodiment, the cervical plate and screw locks form a single cohesive unit wherein each screw lock is embedded within the cervical plate such that a portion of the screw lock extends into certain of the bone screw holes that are formed in the cervical plate adjacent to the screw lock. In the preferred embodiment, each screw lock is configured to engage with one or more bone screws in order to prevent the bone screw from reversing out of or otherwise becoming loose from the bone in which the bone screw has been implanted.

According to an embodiment of the present invention, the spinal fusion surgical hardware described herein comprises a cervical plate. In a preferred embodiment, the cervical plate is formed with one or more bone screw holes. Each of the bone screw holes is configured to receive a bone screw. In the preferred embodiment, each bone screw passes through one of the bone screw holes and is anchored into the appropriate portion of the bone. In some embodiments, the bone screw holes are oriented in pairs, wherein the pairs of bone screw holes are aligned in a parallel orientation, respective to one another. In some embodiments, the screw holes may be oriented in alternate arrangements, including, but not limited to, single and triplet formations. One of ordinary skill in the art would appreciate that there are numerous suitable and advantageous arrangements for the screw holes depending on the specific intended use application of the particular cervical plate, and embodiments of the present invention are contemplated for use with any such screw hole arrangements.

According to an embodiment of the present invention, the cervical plate may be flat or curved. In some embodiments where the cervical plate is curved, the cervical plate may be curved along the entirety of the cervical plate, while in other embodiments, only certain portions of the cervical plate may be curved. The cervical plate may be curved along or relative to the longitudinal axis, the lateral axis, or any combination thereof.

According to an embodiment of the present invention, the spinal fusion surgical hardware described herein comprises one or more screw locks. In a preferred embodiment, each screw lock comprises one or more screw locking edges that partially extend into a bone screw hole. The screw locking edge is formed of a compliant material and is configured to engage with a bone screw to prevent the bone screw from reversing out of the bone. In the preferred embodiment, each screw locking edge may be curved to substantially correspond to the curvature of the bone screw hole into which the screw locking edge extends. Similarly, by configuring the screw locking edge with a curve, the screw locking edge can neatly abut the shaft or the head of the bone screw that is inserted into the bone screw hole. In some embodiments, the screw locking edge is further configured with a lip adapted to extend over a portion of the head of a bone screw. In some embodiments, the screw locking edge is configured such that the curve engages with a side portion of the bone screw head and the lip extends over a top portion of the bone screw head. In a preferred embodiment, the screw locking edge is further configured with one or more prongs that overhang from the top of the screw lock. In the preferred embodiment, the one or more prongs are designed to extend overtop of the head of the bone screw when the bone screw is inserted into the bone screw hole.

In embodiments of the screw lock with two or more screw locking edges, the screw locking edges may be connected together by a compliant middle section comprising one or more linking members. In embodiments with two or more linking members, the linking members may define at least one void formed in the middle of the screw lock. In some embodiments, the voids between the screw locking edges may be nonuniform. For example, the borders of a void may be defined by the contour of the linking members and the screw locking edges. In some embodiments, the linking members may be straight or curved. In some embodiments, the linking members may include bends or depressions. Furthermore, the linking members may be connected to each other by binding members.

According to an embodiment of the present invention, the screw lock may be further configured with one or more plate stop tabs. The plate stop tabs are protrusions on the screw lock that are configured to prevent the screw lock from moving from its embedded position in the cervical plate, especially when the bone screw is being locked into place. In particular, the plate stop tabs resist movement of the screw lock and prevent the screw lock from being pushed through the cervical plate and over an adjacent bone screw hole. In a preferred embodiment, the plate stop tabs are projections that extend beyond each end of the screw locking edge.

According to an embodiment of the present invention, the screw lock is formed from a compliant material. As a bone screw in inserted through a bone screw hole in the cervical plate, the screw lock deforms, wherein the screw locking edge of the screw lock is pushed sufficiently aside to allow the bone screw to pass by the screw lock and through the bone screw hole. Once the bone screw passes the screw lock, the compliant, spring-like functionality of the screw lock causes the screw lock to substantially regain its original form, wherein the screw locking edge moves over the top of the inserted bone screw, thereby securing the bone screw in place and preventing the bone screw from reversing out.

According to an embodiment of the present invention, the screw lock is formed inside the cervical plate using three-dimensional printing. The use of three-dimensional printing prevents the screw lock from separating from cervical plate, while also providing support when forces are applied by the bone screw. In a preferred embodiment, the plate stop tabs formed on the screw lock, as well as the void formed in the middle of the screw lock, engage with the cervical plate to resist unwanted movement of the screw lock within the cervical plate.

Furthermore, by having the screw lock embedded in the cervical plate, the bone screw does not protrude from, or cause a break in, the otherwise substantially smooth surface of the cervical plate. Therefore, embedding the screw lock in the cervical plate reduces the likelihood of irritation or damage to surrounding tissues by the screw lock.

According to an embodiment of the present invention, the screw lock is configured to secure a bone screw without the use of a tool or additional locking step by the surgeon. In a preferred embodiment, and as referenced above, the screw lock is compliant and will flex out of the path of an inserted bone screw. Once the bone screw passes beyond the screw lock, the screw lock will flex back to its original shape, leaving the screw lock abutting the bone screw shaft or above the bone screw head. This feature enables a surgeon to complete operations more quickly and reduces the number of tools needed to secure all of the hardware being implanted during the surgical procedure.

According to an exemplary embodiment of the present invention, a cervical plate assembly comprises a plate body having an anterior surface and a posterior surface opposite the anterior surface, the plate body further comprising: at least a pair of bone screw holes extending through the plate body from the anterior surface through the posterior surface, each of the bone screw holes having a substantially circular side wall, with a screw lock receiving channel extending between and connecting a first screw hole and a second screw hole, and a screw lock body located in the screw lock receiving channel having a first screw locking edge connected by at least one compliant linking member to a second screw locking edge, wherein the first screw locking edge partially extends into a first bone screw hole and the second screw locking edge partially extends into a second screw hole, and wherein each screw locking edge engages with a bone screw and secures the bone screw to the plate body.

According to an exemplary embodiment of the present invention, a cervical plate assembly comprises a plate body having an anterior surface and a posterior surface opposite the anterior surface, the plate body further comprising: at least a pair of bone screw holes extending through the plate body from the anterior surface through the posterior surface, each of the bone screw holes having a substantially circular side wall, with a screw lock receiving channel extending between and connecting a first screw hole and a second screw hole, and a screw lock body located in the screw lock receiving channel having a first screw locking edge connected to a second screw locking edge by a compliant linking member comprised of two serpentine elements, wherein the first screw locking edge partially extends into a first bone screw hole and the second screw locking edge partially extends into a second screw hole, and wherein each screw locking edge engages with a bone screw and secures the bone screw to the plate body.

According to an exemplary embodiment of the present invention, a screw lock assembly comprises a screw lock body having a first screw locking edge connected to a second screw locking edge by a compliant linking member comprised of two serpentine elements, wherein each screw locking edge includes a plate stop tab, wherein the first screw locking edge partially extends into a first bone screw hole and the second screw locking edge partially extends into a second screw hole, and wherein each screw locking edge engages with a bone screw and secures the bone screw to a cervical plate body.

Figure 5:
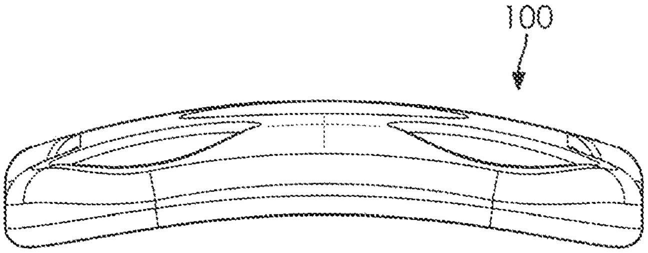
FIG. 5 is a front view of a cervical plate with a screw lock, in accordance with an embodiment of the present invention.
Figure 6:
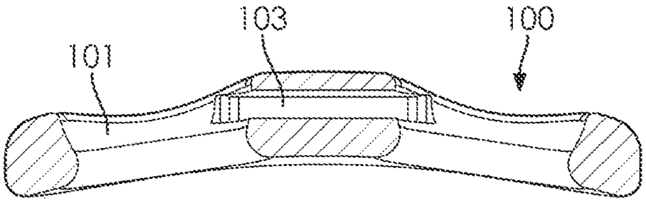
FIG. 6 is a cross-sectional view of a cervical plate with a screw lock, in accordance with an embodiment of the present invention.
Figure 7:
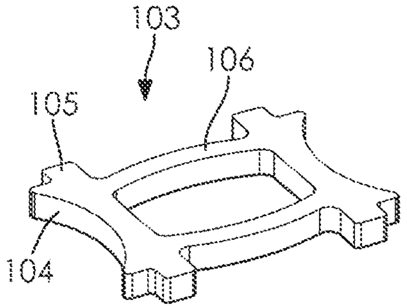
FIG. 7 is a top perspective view of a screw lock, in accordance with an embodiment of the present invention.
Figure 8:
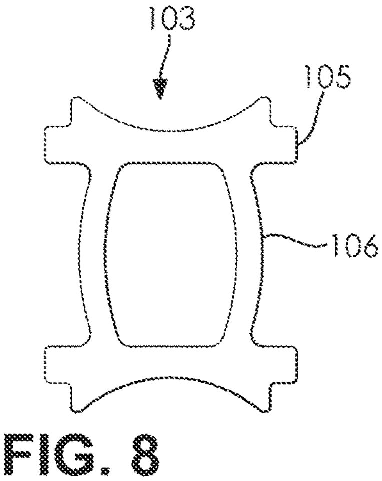
FIG. 8 is a top view of a screw lock, in accordance with an embodiment of the present invention.
Figure 9:
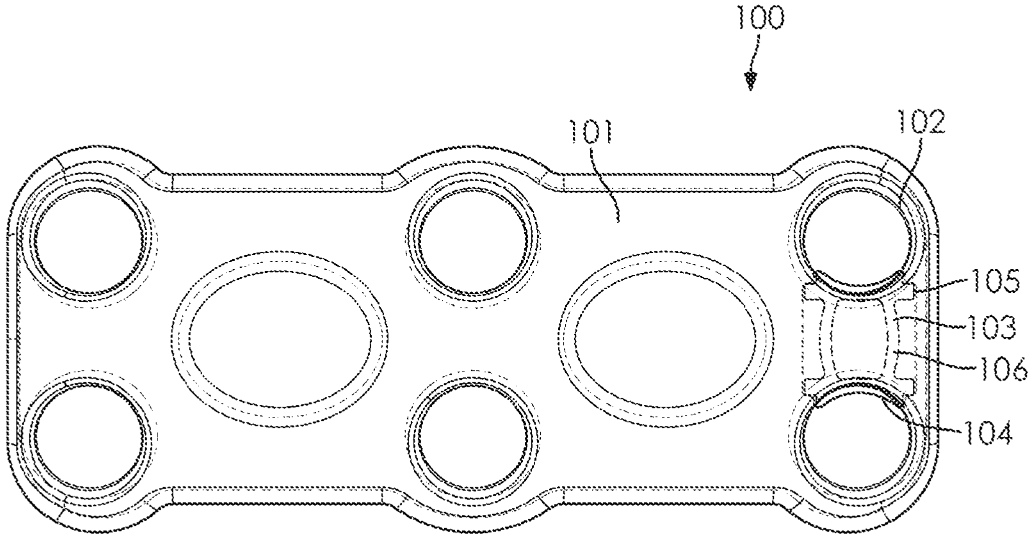
FIG. 9 is bottom view of a transparent cervical plate showing the placement of a screw lock, in accordance with an embodiment of the present invention.
Figure 10:
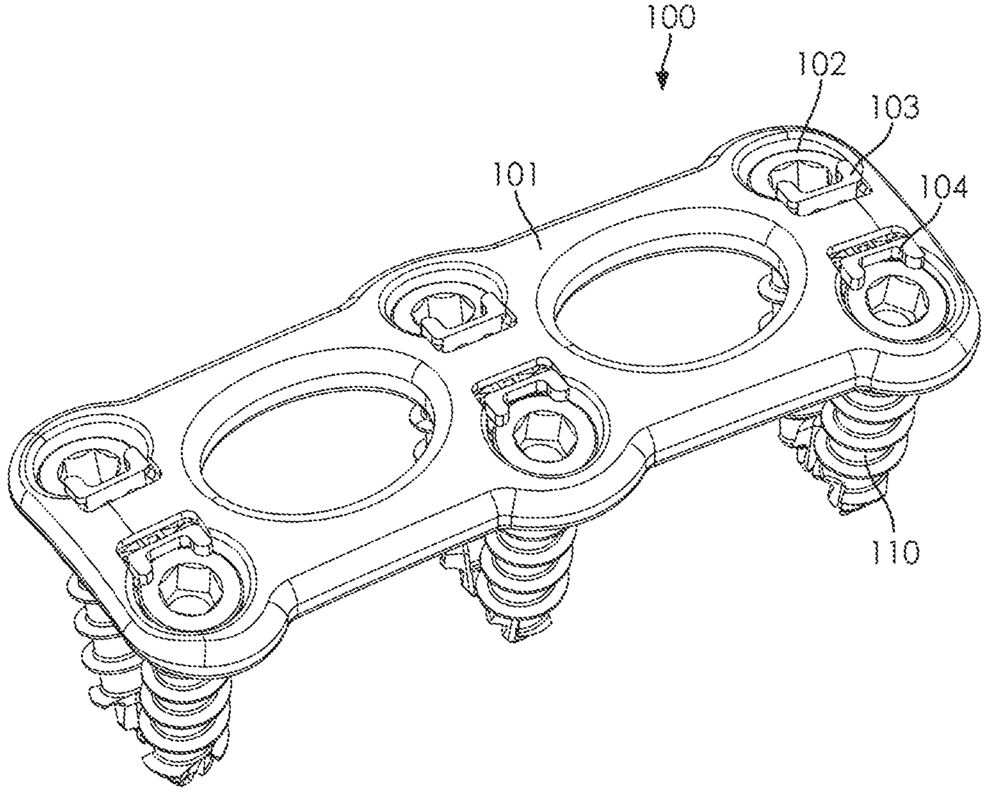
FIG. 10 is a top perspective view of a cervical plate with screw locks and bone screws, in accordance with an embodiment of the present invention.
Figure 11:
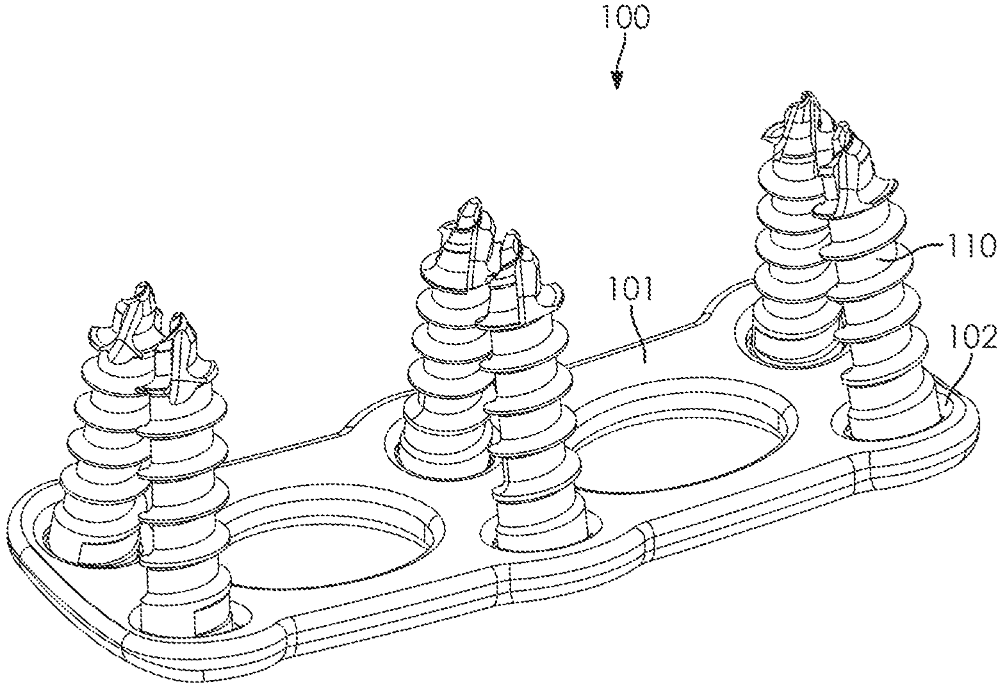
FIG. 11 is a bottom perspective view of a cervical plate with screw locks and bone screws, in accordance with an embodiment of the present invention.
Figure 12:
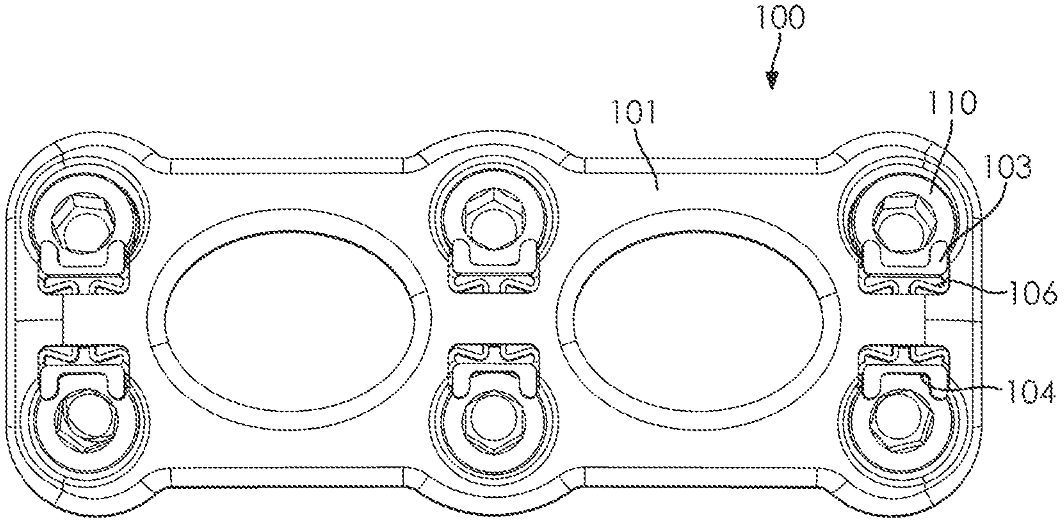
FIG. 12 is a top view of a cervical plate with screw locks and bone screws, in accordance with an embodiment of the present invention.
Figure 13:
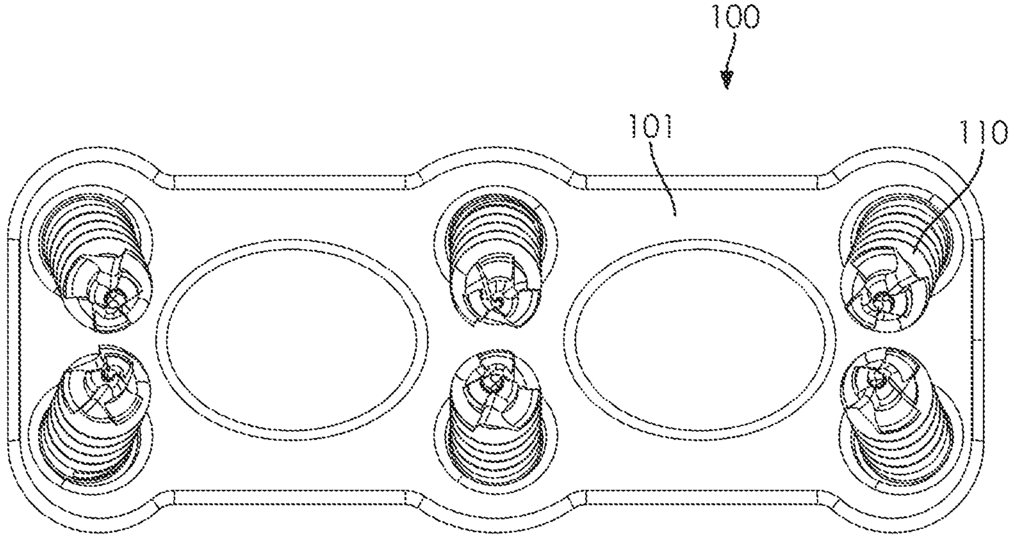
FIG. 13 is a bottom view of a cervical plate with bone screws, in accordance with an embodiment of the present invention.
Figure 14:
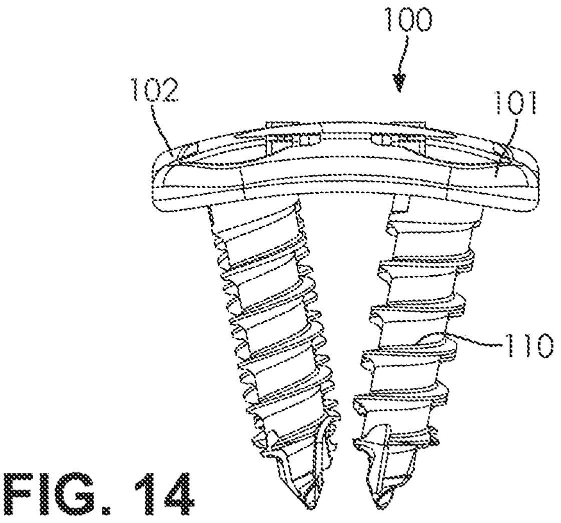
FIG. 14 is a front view of a cervical plate with bone screws, in accordance with an embodiment of the present invention.
Figure 15:
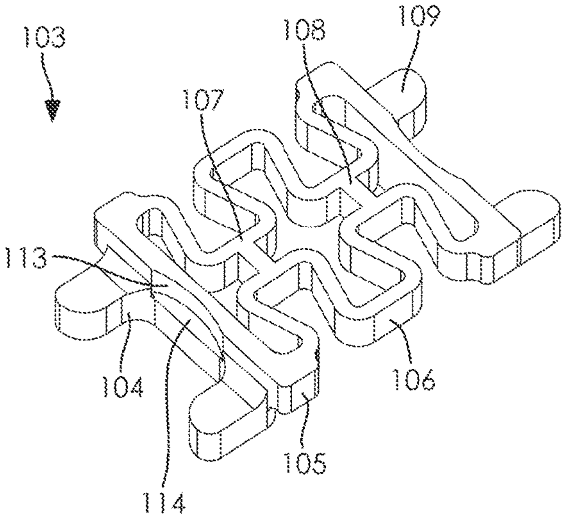
FIG. 15 is a bottom perspective view of a screw lock, in accordance with an embodiment of the present invention.
Figure 16:
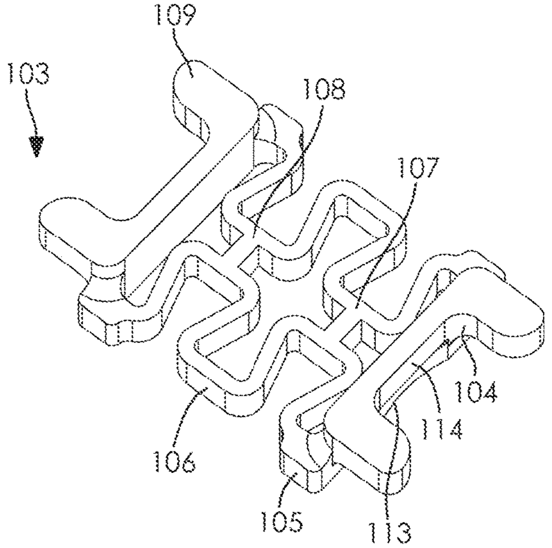
FIG. 16 is a top perspective view of a screw lock, in accordance with an embodiment of the present invention.
Figure 17:
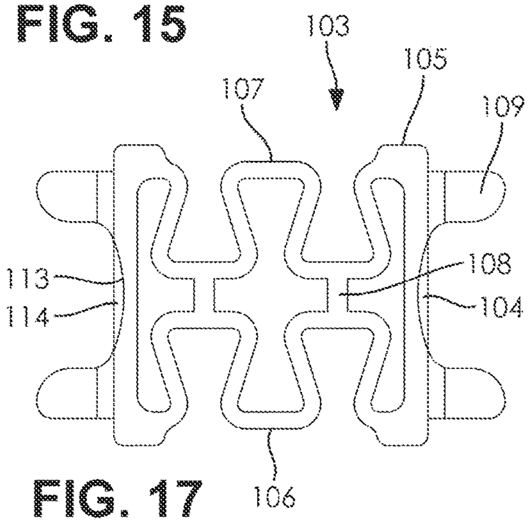
FIG. 17 is a bottom view of a screw lock, in accordance with an embodiment of the present invention.
Figure 18:
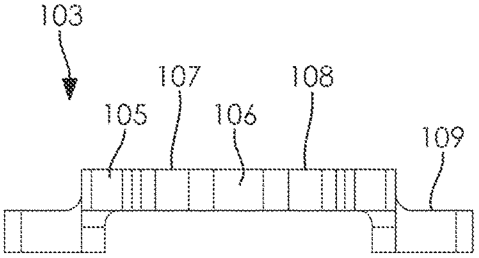
FIG. 18 is a side view of a screw lock, in accordance with an embodiment of the present invention.
Figure 19:
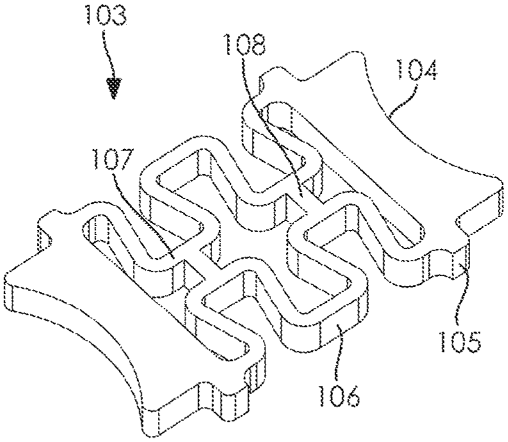
FIG. 19 is a top perspective view of a screw lock, in accordance with an embodiment of the present invention.
Figure 20:
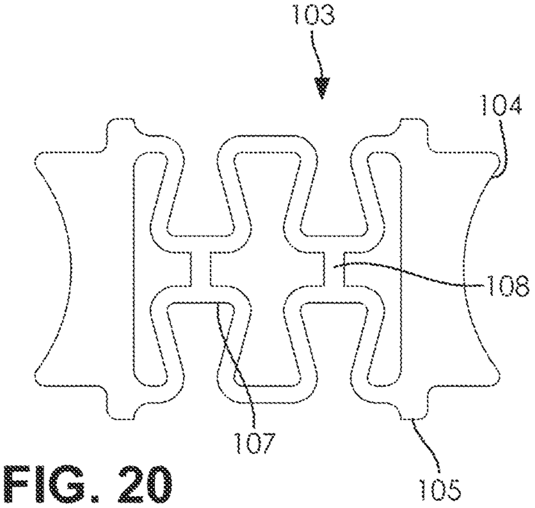
FIG. 20 is top view of a screw lock, in accordance with an embodiment of the present invention.

Turning to FIGS. 1-6, a cervical plate with integrated screw lock, in accordance with an embodiment of the present invention, is shown. In a preferred embodiment, the cervical plate with integrated screw 100 lock includes a cervical plate body 101, a plurality of bone screw holes 102, and at least one screw lock 103. In some embodiments, the screw locks 103 are formed with one or more screw locking edges 104 (as shown in FIGS. 7-9). In some embodiments, the screw locks 103 are formed with one or more plate stop tabs 105 (as shown in FIGS. 7-9). At least one screw lock 103 may be retained in the cervical plate body 101, within a screw lock receiving channel 112. In some embodiments, the screw lock receiving channel 112 is substantially hollow and is configured to stabilize the position of the screw lock 103. As is shown in FIG. 5, in an exemplary embodiment, the cervical plate body 101 is curved.

Turning now to FIGS. 7-8, an integrated screw lock 103, in accordance with embodiments of the present invention, is shown. In an exemplary embodiment, the screw lock 103 has curved screw locking edges 104 to substantially correspond to the curvature of the bone screw hole 102 into which the screw locking edge 104 extends.

As shown in FIGS. 15-18, the screw locking edges 104 may include an indent 113, to substantially correspond to the curvature of a bone screw 110. The screw locking edge 104 may be further configured with a lip 114 adapted to extend over a portion of the head of a bone screw 110. In some embodiments, the indent 113 is configured to engage with a side portion of a bone screw head and the lip 114 is configured to extend over a top portion of the bone screw head. The screw lock 103 may be configured to accommodate both variable and fixed angled bone screws 110. The screw lock 103 is also preferably configured with one or more plate stop tabs 105 designed to prevent the screw lock 103 from moving from its embedded position in the cervical plate body 100 (as shown in FIG. 9). The plate stop tabs 105 are particularly useful when the bone screw 110 is being locked into place.

As further shown in FIGS. 15-18, in some embodiments, the screw locking edge is configured with one or more screw lock prongs 109 that overhang from the screw lock 103. In the preferred embodiment, the one or more prongs 109 are designed to extend overtop of the head of the bone screw 110 and hold the bone screw 110 in place once the bone screw 110 has been inserted into the bone screw hole 102. The plate stop tabs 105 may be configured to resist movement of the screw lock 103 and prevent the screw lock 103 from being pushed through the cervical plate body 100 and over an adjacent bone screw hole 102 (as shown in FIG. 9). In some embodiments, the plate stop tabs 105 are projections that extend beyond each end of the screw locking edge 104.

As shown in FIGS. 15-20, according to embodiments of the present invention, the screw locking edges 104 may be connected together by a compliant middle section comprising one or more compliant linking members 106. In some embodiments, the linking member 106 may define at least one void formed in the middle of the screw lock 103. In some embodiments, the voids between the screw locking edges 104 may be nonuniform. For example, the borders of a void may be defined by the contour of the linking member 106 and the screw locking edges 104. In some embodiments, the linking member 106 may be straight or curved. In some embodiments, the linking member 106 may include bends or depressions 107. Furthermore, a first linking member 106 may be connected to a second linking member 106 by one or more binding members 108. In some embodiments, the compliant linking members 106 are configured in a serpentine shape. In some embodiments, the two serpentine elements are connected by one or more binding members 108.

Figure 21:
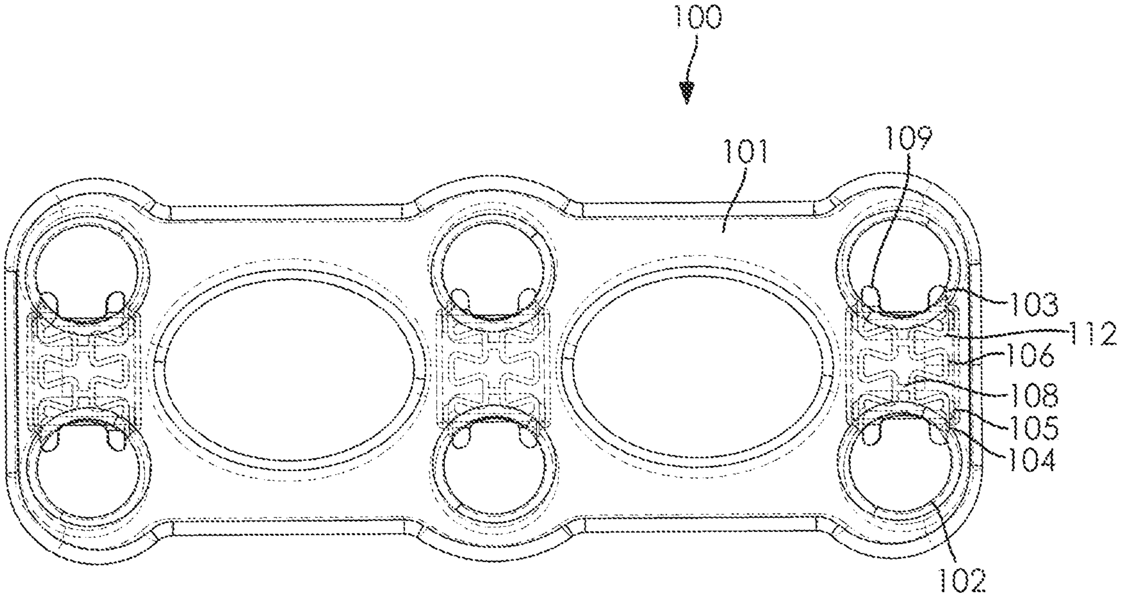
FIG. 21 is a bottom view of a transparent cervical plate showing the placement of a screw lock, in accordance with an embodiment of the present invention.

Turning now to FIG. 9 and FIG. 21, a bottom view of a cervical plate and integrated screw lock with a transparent cervical plate, in accordance with a preferred embodiment of the present invention, is shown. In a preferred embodiment, the screw lock 103 is formed of a compliant material.

As demonstrated in FIGS. 10-14, a bone screw 110 may be inserted through a bone screw hole 102 in the cervical plate body 101, deforming the screw lock 103, such that the screw locking edge 104 of the screw lock 103 is pushed sufficiently aside to allow the bone screw 110 to pass by the screw lock 103 and through the bone screw hole 102. Once the bone screw 110 passes the screw lock 103, the compliant, spring-like functionality of the screw lock 103 causes the screw lock 103 to substantially regain its original form, wherein the screw locking edge 104 neatly abuts the shaft or the head of the bone screw 110, thereby securing the bone screw 110 in place and preventing the bone screw 110 from reversing out. In some embodiments, the screw locking edge 104 engages with a designated groove 111 on the bone screw 110 to secure the bone screw 110 in place to prevent the bone screw 110 from reversing out.

The terminology used herein is for the purpose of describing particular embodiments only and is not intended to be limiting of the invention. As used herein, the term “and/or” includes any and all combinations of one or more of the associated listed items. It will further be understood that the terms “comprises” and/or “comprising,” when used in this specification, specify the presence of stated features, steps, operations, elements, and/or components, but do not preclude the presence or addition of one or more other features, steps, operations, elements, components, and/or groups thereof.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

The invention claimed is:

1. A screw lock for a cervical plate assembly, the screw lock comprising:
- a first screw locking edge at a first end of the screw lock and a second screw locking edge at a second end of the screw lock, wherein each of the screw locking edges has an outer side edge and an inner side edge opposite the outer side edge;
- a compliant middle section comprising a first linking member and a second linking member that extend between the inner side edge of the first locking edge and the inner side edge of the second locking edge; and
- one or more binding members fixed between the first and second linking members, wherein each of the one or more binding members are spaced along the linking members between the inner side edge of the first screw locking edge and the inner side edge of the second screw locking edge.

2. The screw lock of claim 1, wherein each of the linking members is serpentine with one or more inward bends that extend toward a medial line of the screw lock body that is perpendicular to the first and second screw locking edges.

3. The screw lock of claim 1, wherein the binding members are shorter in length than the inner side edge of each of the first and second screw locking edges.

4. The screw lock of claim 1, wherein the one or more binding members include at least a first binding member and a second binding member.

5. The screw lock of claim 4, wherein the first binding member is parallel to the second binding member.

6. The screw lock of claim 4, further comprising a plurality of voids defined by combinations of the inner side edges of the first and second screw locking edges, the first and second linking members, and the first and second binding members, including at least a central void defined by the first and second linking members and the first and second binding members.

7. The screw lock of claim 1, further comprising a first pair of plate stop tabs formed where the linking members attach to the first screw locking edge and a second pair of plate stop tabs formed where the linking members attach to the second screw locking edge.

8. The screw lock of claim 7, wherein each plate stop tab of the first and second pairs of plate stop tabs has a distal end extending perpendicularly relative to a medial line of the screw lock, the medial line being perpendicular to the first and second screw locking edges.

9. The screw lock of claim 8, wherein the distal end of each the plate stop tab of the first and second pairs of plate stop tabs extends further from the medial line than any point of the first and second linking members.

10. The screw lock of claim 1, wherein the outer side edge of screw locking edge comprises two prongs that are cantilevered from the compliant middle section.

11. The screw lock of claim 1, wherein an indentation and lip are formed between the two prongs on a bottom side of the outer side edge of the screw locking edge.

12. A screw lock for a cervical plate assembly, the screw lock comprising:
- a first screw locking edge at a first end of the screw lock and a second screw locking edge at a second end of the screw lock, wherein each of the screw locking edges has an outer side edge and an inner side edge opposite the outer side edge;
- a compliant middle section comprising a first linking member and a second linking member extending between the inner side edge of the first locking edge and the inner side edge of the second locking edge; and
- a first pair of plate stop tabs formed where the linking members attach to the first screw locking edge and a second pair of plate stop tabs formed where the linking members attach to the second screw locking edge, wherein each plate stop tab of the first and second pairs of plate stop tabs has a distal end extending perpendicularly relative to a medial line of the screw lock, the medial line being perpendicular to the first and second screw locking edges.

13. The screw lock of claim 12, wherein the distal end of each of the plate stop tabs of the first and second pairs of plate stop tabs extends further from the medial line than any point of the first and second linking members.

14. The screw lock of claim 12, further comprising one or more binding members connecting the first and second linking members.

15. The screw lock of claim 14, wherein each of the one or more binding members are spaced along the linking members between the inner side edge of the first screw locking edge and the inner side edge of the second screw locking edge.

16. The screw lock of claim 15, wherein each of the linking members is serpentine with one or more inward bends that extend toward a medial line of the screw lock body that is perpendicular to the first and second screw locking edges.

17. The screw lock of claim 16, wherein the binding members connect the inward bends of the linking members at an apex of the inward bends.

18. The screw lock of claim 15, wherein the binding members are shorter in length than the inner side edge of each of the first and second screw locking edges.

19. The screw lock of claim 15, wherein the one or more binding members include at least a first binding member and a second binding member that are parallel.

20. A screw lock for a cervical plate assembly, the screw lock comprising:

a first screw locking edge at a first end of the screw lock and a second screw locking edge at a second end of the screw lock, wherein each of the screw locking edges has an outer side edge and an inner side edge opposite the outer side edge;

a compliant middle section comprising a first linking member and a second linking member that extend between the inner side edge of the first locking edge and the inner side edge of the second locking edge, wherein each of the linking members is serpentine with one or more inward bends that extend toward a medial line of the screw lock body that is perpendicular to the first and second screw locking edges;

one or more binding members fixed between the first and second linking members, wherein each of the one or more binding members are spaced along the linking members between the inner side edge of the first screw locking edge and the inner side edge of the second screw locking edge; and a first pair of plate stop tabs formed where the linking members attach to the first screw locking edge and a second pair of plate stop tabs formed where the linking members attach to the second screw locking edge, wherein each plate stop tab of the first and second pairs of plate stop tabs has a distal end extending perpendicularly away from the medial line.

* * * * *